United States Patent
Geller et al.

(10) Patent No.: US 9,390,236 B2
(45) Date of Patent: Jul. 12, 2016

(54) RETRIEVING AND VIEWING MEDICAL IMAGES

(75) Inventors: Dieter Geller, Aachen (DE); Reinhard Kneser, Aachen (DE); Yuechen Qian, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 597 days.

(21) Appl. No.: 13/320,956

(22) PCT Filed: May 17, 2010

(86) PCT No.: PCT/IB2010/052174
§ 371 (c)(1),
(2), (4) Date: Nov. 17, 2011

(87) PCT Pub. No.: WO2010/134016
PCT Pub. Date: Nov. 25, 2010

(65) Prior Publication Data
US 2012/0066241 A1    Mar. 15, 2012

(30) Foreign Application Priority Data
May 19, 2009  (EP) .................................... 09160574

(51) Int. Cl.
*G06F 17/30*    (2006.01)
*G06F 19/00*    (2011.01)

(52) U.S. Cl.
CPC .......... *G06F 19/3487* (2013.01); *G06F 19/321* (2013.01); *G06F 19/324* (2013.01)

(58) Field of Classification Search
CPC ..................... G06F 17/30244; G06F 17/30861
USPC ........ 707/759, 737; 382/128; 705/3; 345/424
See application file for complete search history.

(56) References Cited

U.S. PATENT DOCUMENTS 5,825,909 A    10/1998  Jang
6,154,879 A    11/2000  Pare, Jr. et al.
(Continued)

FOREIGN PATENT DOCUMENTS

JP    2002541533 A    12/2002
JP    2008516472       5/2008
(Continued)

OTHER PUBLICATIONS

By Shih-Fu Chang et al; "Multimedia Search and Retrieval" Published as a chapter in Advances in Multimedia: Systems, Standards, and Networks, A. Puri and T. Chen (eds.). New York: Marcel Dekker, 1999. pp. 1-28.
(Continued)

*Primary Examiner* — Hosain Alam
*Assistant Examiner* — Robert F May

(57) ABSTRACT

As medical imaging becomes more affordable, and the diversity of diagnostic modalities and therapeutic treatments increase, the amount of data being stored increases, and the problem becomes even more critical. One approach to improve retrieval efficiency of images is to employ semantics to establish a defined set of search and classification terms. However, such semantic systems still require the user to make a selection of the most appropriate term or terms to classify a report or image, and the accuracy of the results are thus dependent on the skill and knowledge of the classifier. According to a first aspect of the invention, a retriever is provided for retrieving a medical image having a searchable attribute, the retriever being configured to interface with a semantic database and an image database, and wherein the searchable attribute is determined by segmenting the medical image, using the anatomical model.

14 Claims, 7 Drawing Sheets

(56) References Cited

U.S. PATENT DOCUMENTS

| | | | |
|---|---|---|---|
| 6,563,959 B1 | 5/2003 | Troyanker | |
| 8,150,120 B2 * | 4/2012 | Gindele | G06T 7/0081 345/424 |
| 2001/0051881 A1 | 12/2001 | Filler | |
| 2004/0101177 A1 * | 5/2004 | Zahlmann | G06F 17/30247 382/128 |
| 2005/0049500 A1 | 3/2005 | Babu et al. | |
| 2006/0285734 A1 * | 12/2006 | Haider | A61B 5/055 382/128 |
| 2007/0130165 A1 * | 6/2007 | Sjoblom | G06F 19/321 |
| 2007/0160275 A1 * | 7/2007 | Sathyanarayana | G06F 17/30265 382/128 |
| 2008/0010092 A1 * | 1/2008 | Smirniotopoulos | G06F 19/321 705/3 |
| 2008/0027917 A1 * | 1/2008 | Mukherjee | G06F 17/30247 |
| 2008/0140722 A1 * | 6/2008 | Jakobovits | G06F 19/321 |
| 2009/0132285 A1 | 5/2009 | Jakobovits | |
| 2009/0183248 A1 | 7/2009 | Tuyls et al. | |
| 2009/0192824 A1 * | 7/2009 | Minakuchi | G06F 19/321 705/3 |
| 2009/0279754 A1 * | 11/2009 | Gindele et al. | 382/128 |
| 2010/0027784 A1 | 2/2010 | Tuyls et al. | |
| 2010/0293164 A1 * | 11/2010 | Weese | G06F 19/321 707/737 |

FOREIGN PATENT DOCUMENTS

| | | |
|---|---|---|
| JP | 2008526080 A | 7/2008 |
| WO | 0233577 A1 | 4/2002 |

OTHER PUBLICATIONS

By M. Flickner et al; "Query by Image and Video Content: The QBIC System" IBM Almaden Research Center; Sep. 1995; pp. 23-32.

By D. Racoceanu et al; "A Semantic Fusion Approach Between Medical Images and Reports Using UMLS" 1 IPAL-Image Perception, Access and Language—UMI-CNRS 2955 Institute for Infocomm Research, A*STAR, Singapore {visdaniel, viscl, sturot}@i2r.a-star.edu.sg http:/www.i2r.a-star.edu.sg/2 University of Franche-Comte, Besancon, France 3 "Politehnica" University from Timisoara, Romania 4 Ecole Nationale Superieure de Mecaniques et Microtechniques de Besancon, France'; Asia Information Retrieval Symposium (AIRS) Oct. 26-28, 2006, Proceedings; pp. 460-475.

By Ramaswamy; MoSearch: A Radiologist-Friendly Tool for Finding Based Diagnostic Report and Image Retrieval (RSNA 1996); Radiographics 1996; pp. 923-933.

* cited by examiner

380

MRI ORBIT WITH CONTRAST

CLINICAL INFORMATION:
99 year old with tumor on left side by |optic nerve.| Has began to notice vision lost.

232

COMPARISON:
Prior study dated October 00, 0000

221

PROCEDURE:
The T1 and T2 and enhanced T1-weighted images of the orbits in multiple planes.

Contrast: 10 ml of Magnevist administered intravenously

FINDINGS:
Again seen is a mass involving the floor of the anterior cranial fossa on the left along the medial margin of the sphenoid wing. The mass is a dural-based with a dural tail. This is consistent with a meningioma. The mass measures 12 mm in greatest diameter. There does not appear to be involvement of the optic nerve. The optic nerves shows no convincing evidence of enhancement

231

233

The extraocular muscles and ▓▓▓▓▓▓▓ are unremarkable in appearance. The globes have a normal contouring configuration. The cavernous sinus appears normal. The pituitary gland and pituitary stalk appear normal.

234

IMPRESSION:
1. Dural-based lesion involving the floor of the anterior cranial fossa on the left

FIG. 6B

RETRIEVING AND VIEWING MEDICAL IMAGES

FIELD OF THE INVENTION

The invention relates to retrieving and classifying medical images, and to classifying medical reports.

BACKGROUND OF THE INVENTION

As medical image acquisition systems become more prevalent, many healthcare professionals, such as radiologists and physicians, face the problem that the time available for the examination of the images decreases. Consequently, there is a growing need for diagnosis support systems to assist in the examination.

One of the tools commonly used is to access records related to previous cases. These records may comprise medical images and textual medical reports. For ease of storage and retrieval, these records are collected in databases which may take many forms, such as local folders on a computer system, accessible to individual users or to multiple users, PACS systems, a reference case manager like mypacs.net (www.mypacs.net).

These databases comprise many reports, far exceeding the number of cases that any single person can recall. Even a personal folder, populated by one healthcare professional such as a radiologist, will typically grow beyond the point where its user can recall its full content. The problem is compounded by the access to databases of multiple users and multiple healthcare disciplines. The ability to search the databases and retrieve relevant medical images therefore becomes increasingly important. As medical imaging becomes more affordable, and the diversity of diagnostic modalities and therapeutic treatments increase, the amount of data being stored increases, and the problem becomes even more critical.

One approach to improve retrieval efficiency of images is to employ semantics to establish a defined set of search and classification terms. Such semantics systems include UMLS (Unified Medical Language System) and Radlex (a lexicon for retrieval of radiology information resources). However, such semantics systems still require the user to make a selection of the most appropriate term or terms to classify a report or image, and the accuracy of the results are thus dependent on the skill and knowledge of the classifier.

An attempt at a semantic indexing system for medical reports and medical images is disclosed in "A Semantic Fusion Approach Between Medical Images and Reports Using ULMS", Racoceanu, Lacoste, Teodorescu, Vuillemenot, Third Asia Information Retrieval Symposium, AIRS 2006, Singapore, Oct. 16-18, 2006. This system indexes reports by determining the frequency of semantic concepts in the text and applying a weighting appropriately. Images are indexed by first defining a visual vocabulary and then optionally weighting the semantic concepts depending on where they are found in the image. For example, a semantic concept detected in the centre of an image is considered more important. The visual vocabulary is a visual representation in terms of color, texture and shape, which is to be searched for in the image records.

Unfortunately, creating the visual vocabulary requires a great deal of user guidance in selecting the images.

SUMMARY OF THE INVENTION

It is an object of the invention to provide a system and method for retrieving a medical image (310) having a searchable attribute. It is a further object of the invention to provide a system and method for assigning a searchable attribute to a medical image.

The invention is defined by the independent claims. Advantageous embodiments are defined in the dependent claims.

According to a first aspect of the invention, a retriever is provided for retrieving a medical image having a searchable attribute, the retriever being configured to interface with:

a semantic database configured to store and provide anatomical semantics, and an image database configured to store and provide the medical image, wherein the searchable attribute is determined by:

retrieving an anatomical model comprising a label associated with an anatomical structure;

determining the presence of the anatomical structure by segmenting the medical image using the anatomical model;

retrieving anatomical semantics from the semantic database, and determining a relevant semantic for the anatomical structure, based upon the label;

the retriever comprising:

a user interface for providing a user selection, and a processor configured to:

receive the user-selection of one of the anatomical semantics, and retrieve the medical image using the user-selected semantic and the searchable attribute.

The invention is based upon the insight that the classification of images may be improved by segmenting the images, using anatomical models comprising anatomical labels. If the segmentation determines the presence of an anatomical structure, the appropriate label in the model may be used to determine the appropriate semantic. It is this semantic which is used as the searchable attribute for the image, providing a standardized dictionary for classification and searching. Therefore, a higher degree of relevant hits will be provided when the user uses an anatomical semantic in his query.

These anatomical models with anatomical labels are widely available for the many different modalities of medical image acquisition. It is therefore not required for the user to spend time selecting training images. In addition, the use of models gives a more accurate detection of anatomical structures, because they can deform to individual anatomical parts and spatial relations between anatomical parts, even in 3D.

In another aspect of the invention, the retrieved medical image has a viewing attribute, and the display is configured to provide the user with the representation of the medical image according to the viewing attribute.

For a healthcare professional, viewing images is a time-consuming task. This aspect of the invention is based upon the insight that a large portion of time used for viewing images is actually used to set up the view—for example, scrolling through a data volume to find the desired slices, locating the object-of-interest on the image, selecting the viewing angle, selecting the correct scaling/rotation, selecting the correct initial zoom. The invention reduces this time by providing viewing attributes which the user may enter, or the retriever may be configured to automatically load and execute the attributes when the associated medical image is retrieved.

An additional advantage is available when an image comprises more than one object-of-interest. Using the invention, the medical image may even be associated with a plurality of searchable attributes, with each one having a viewing attribute.

The user may be provided with a catalogue of the semantic system to be used as a reference when constructing his queries. However, such an open system is prone to errors of transcription and using incorrect terms.

In a further aspect of the invention, the display is further configured to provide the user with a representation of the anatomical semantics, and the user interface is further configured to allow the user to select one or more of the anatomical semantics. For example, this representation may be in the form of a menu.

This has the advantage that the user can select one or more of the semantics used for the classification, reducing the risk of error.

In another aspect of the invention, the representation comprises the text of a medical report wherein one or more anatomical semantics are distinguished for the user from the rest of the text.

This provides the user with an intuitive interface, i.e. upon opening a report, semantic terms are distinguished in some way so that the user may select them as required. This is particularly advantageous as the user is only presented with relevant semantics.

In another aspect of the invention, the user interface is configured to provide the medical report, and the processor is further configured to:
  receive the medical report;
  retrieve anatomical semantics from the semantic database, and
  search the medical report for anatomical semantics and distinguish the semantics found in the text.

This provides the user with the possibility to process his own reports with the system, so that the semantics are distinguished in the text. These reports may then be added to the report database for future retrieval, or the report may be used immediately for retrieving images when the distinguished semantics are selected.

Alternatively, in another aspect of the invention, the retriever is further configured to interface with a report database, configured to store and provide medical reports including text wherein one or more anatomical semantics are distinguished for the user from the rest of the text, and the processor is further configured to retrieve the medical report from the medical report database.

The user may use the system to retrieve an earlier stored report in which the semantic terms were already distinguished from the rest of the text. Once retrieved, the report may be used for retrieving images when the distinguished semantics are selected.

In another aspect of the invention, a method is provided for retrieving a medical image having a searchable attribute, comprising:
  providing a semantic database configured to store and provide anatomical semantics;
  providing an image database configured to store and provide the medical image;
  determining the searchable attribute of the medical image by:
    retrieving an anatomical model comprising a label associated with an anatomical structure;
    determining the presence of the anatomical structure by segmenting the medical image using the anatomical model;
    retrieving anatomical semantics from the semantic database, and
    determining a relevant semantic for the anatomical structure, based upon the label;
  the method further comprising:
    providing a user selection of one of the anatomical semantics, and
    retrieving the medical image using the user-selected semantic and the searchable attribute.

The retriever of the invention in any of its embodiments may be comprised in a workstation or a medical imaging acquisition apparatus.

In another aspect of the invention, a classifier is provided for assigning a searchable attribute to a medical image, the classifier being configured to interface with:
  an image database configured to store and provide the medical image;
  a semantic database configured to store and provide anatomical semantics;
  a model database configured to store and provide an anatomical model, wherein the anatomical model comprises a label associated with an anatomical structure;
  the classifier comprising a segmenter configured to:
  retrieve an anatomical model comprising a label associated with an anatomical structure from the model database;
  determine the presence of the anatomical structure by segmenting the medical image, using the anatomical model;
  retrieve anatomical semantics from the semantic database;
  determine a relevant semantic for the anatomical structure, based upon the label, and
  store the medical image in the image database, with the determined semantic being the searchable attribute of the medical image.

The invention is based upon the insight that the classification of images may be improved by segmenting the images, using anatomical models comprising anatomical labels, as indicated above. It may be advantageous to separate the functionality of retrieving images and classifying images, as the operations may be performed at different times. A separate classifier may be employed to classify the images in the image database during offline periods such as at night or in the weekend.

In yet another aspect of the invention, the segmenter is further configured to:
  determine the extent of the anatomical structure by segmenting the medical image, using the anatomical model;
  determine a relevant view of the anatomical structure, and
  store the medical image in the image database, with the determined view being a viewable attribute of the medical image.

This aspect of the invention is based upon the insight that a large portion of time used for viewing images is actually used to set up the view, as described above. In particular, the use of anatomical models means that the extent of the object-of-interest may be determined by the segmenter and used to define viewing attributes. For example, the position and the extent of the object-of-interest may be used to define viewing coordinates and an initial zoom.

In a still further aspect of the invention, the classifier is further configured to:
  interface with a report database, configured to store and provide medical reports;
  the classifier further comprising a distinguisher configured to:
  retrieve a medical report from the medical report database;
  retrieve anatomical semantics from the semantic database;
  search the medical report for anatomical semantics and distinguish the semantics found in the text, and
  store the medical report having distinguished semantics in the medical report database.

Although the function of the distinguisher may be implemented separately, or integrated into the retriever as described above, it may be advantageous to include the distinguisher in the classifier. In this way, consistence of the semantic terms used is optimized because classification of the images and detection of semantic terms in reports is performed by proximate functional units.

The classifier of the invention in any of its embodiments may be comprised in a workstation or a medical imaging acquisition apparatus.

In another aspect of the invention, a method is provided for assigning a searchable attribute to a medical image, the method comprising:

providing an image database configured to store and provide the medical image;

providing a semantic database configured to store and provide anatomical semantics;

providing a model database configured to store and provide an anatomical model, wherein the anatomical model comprises a label associated with an anatomical structure;

retrieving an anatomical model comprising a label associated with an anatomical structure from the model database;

determining the presence of the anatomical structure by segmenting the medical image, using the anatomical model;

retrieving anatomical semantics from the semantic database;

determining a relevant semantic for the anatomical structure based upon the label, and storing the medical image in the image database, with the determined semantic being the searchable attribute of the medical image.

A computer program product is also envisioned for carrying out the methods of the invention when loaded and run on a computer.

In still another aspect of the invention, a method is provided for distinguishing anatomical semantics in a medical report, the method comprising:

providing a report database, configured to store and provide medical reports;

retrieving a medical report from the medical report database;

retrieving anatomical semantics from the semantic database;

searching the medical report for anatomical semantics and distinguishing the semantics found in the text, and storing the medical report having distinguished semantics in the medical report database.

It will be appreciated by those skilled in the art that two or more of the above-mentioned embodiments, implementations, and/or aspects of the invention may be combined in any way deemed useful.

Modifications and variations of the image acquisition apparatus, of the workstation, of the system, and/or of the computer program product, which correspond to the described modifications and variations of the method, can be carried out by a person skilled in the art on the basis of the present description.

It will also be obvious to the skilled person that the invention does not need to be limited to images generated by radiologists. It may be used with any kind of medical imaging data. This imaging data may be acquired by any imaging modality, such as X-ray Imaging, Computed Tomography (CT), Magnetic Resonance Imaging (MRI), Ultrasound (US), Positron Emission Tomography (PET), Single Photon Emission Computed Tomography (SPECT) and Nuclear Medicine (NM).

It is also envisioned that the invention may be used to classify and retrieve any visual information content, such as images on web pages or databases of photographs. In such cases the models used for classifying the images may be created by any means known in the art.

BRIEF DESCRIPTION OF THE DRAWINGS

These and other aspects of the invention are apparent from and will be elucidated with reference to the embodiments described hereinafter.

In the drawings:

FIGS. 6A and 6B depict possible representations of the semantic terms to the user on a display.

The Figures are purely diagrammatic and not drawn to scale. Particularly for clarity, some dimensions are exaggerated strongly. Similar components in the Figures are denoted by the same reference numerals as much as possible.

DETAILED DESCRIPTION OF THE PREFERRED EMBODIMENTS

The invention comprises two functional units, a classifier, described below, and a retriever. The retriever 300 according to the invention, is configured to retrieve images classified by the classifier 600, and the classifier 600 is configured to classify images for retrieval by the retriever 300. Although they are described separately, a system according to the invention is envisioned comprising a retriever 300 and/or a classifier 600. Additionally, one or more of the databases may form part of such a system, may be distinctly separate or partially incorporated in such a system when a database is distributed.

Figure 1:
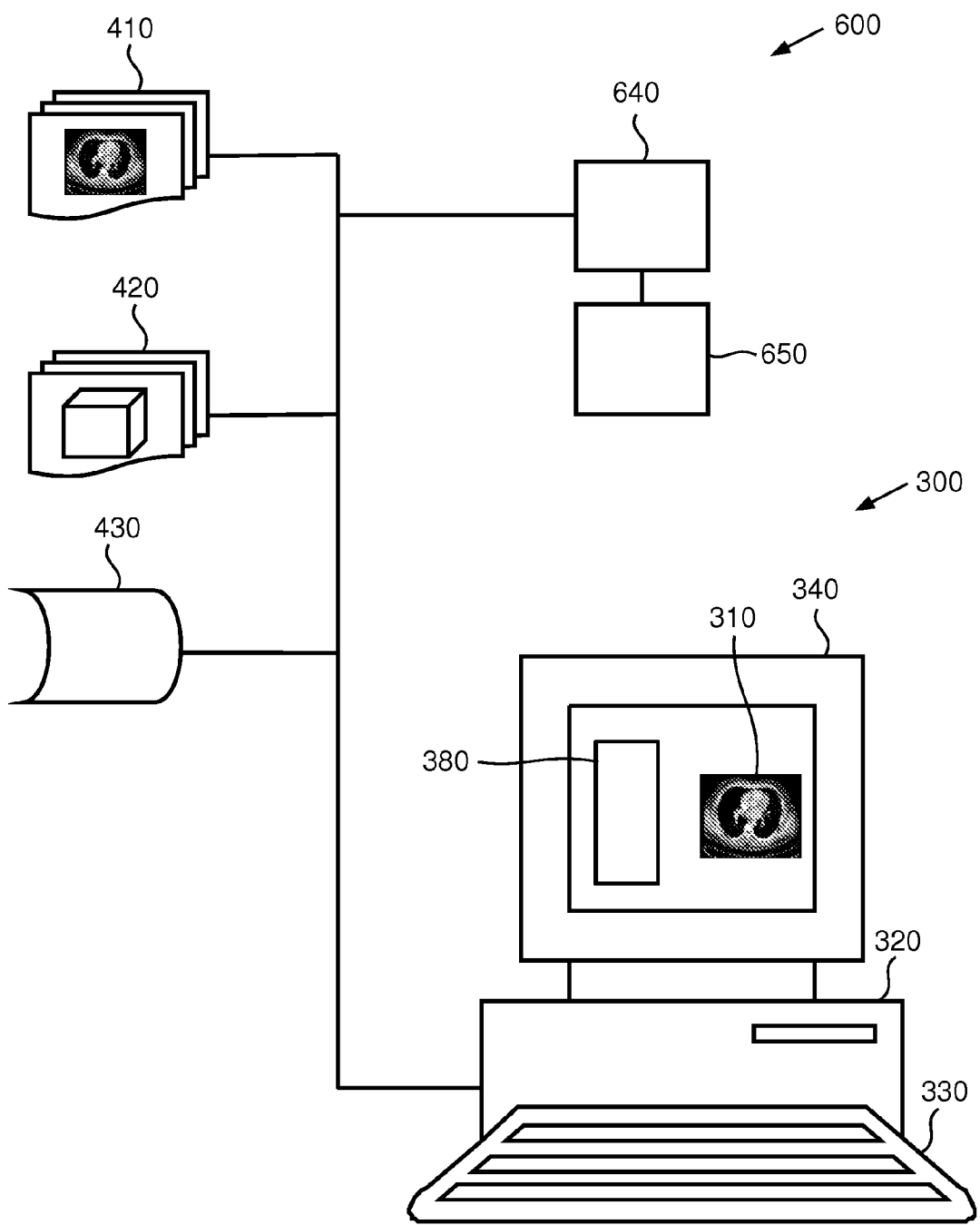
FIG. 1 shows a retriever and classifier according to the invention.

The retriever 300 for retrieving a medical image 310 having a searchable attribute is depicted in FIG. 1. The retriever 300 is configured to interface with a semantic database 430 and an image database 410—any suitable network interface or bus system may be used.

The semantic database 430 is configured to store and provide anatomical semantics in any appropriate way known in the art. For example, the semantics may be in the form of a lexicon, or organized in a hierarchy or ontology. The exact form selected may be selected based upon the skills and knowledge of the users of the retriever. The semantic database 430 provides a standardized and limited terminology used to classify and retrieve the medical images. The semantic database 430 may be local folders comprised in the system 300, accessible to individual users or to multiple users. The semantic database 430 may also be an on-line system, such as UMLS or RadLex, which may be made available by providing the system 300 with an appropriate network connection. The image database 430 may typically also allow deletion and annotations of the reports stored.

The image database 410 is configured to store and provide the medical image 310. The images in the database 410 may be selected based upon the skills and knowledge of the users of the retriever, or the image database 410 may be defined as a sub-set of a much larger database. For example, if the users of the system are radiologists, then the retriever may be interfaced with a generic image database, but only given access to images tagged as radiology images. The image database 410 may be local folders comprised in the system 300, accessible to individual users or to multiple users. The image database 410 may also be an on-line system, such as a PACS system or a reference case manager like mypacs.net which may be made available by providing the system 300 with an appropriate network connection. The image database 410 may typically also allow deletion and annotations of the reports stored.

The searchable attribute of the image to be retrieved is determined by:

retrieving an anatomical model comprising a label associated with an anatomical structure;

determining the presence of the anatomical structure by segmenting the medical image 310 using the anatomical model;

retrieving anatomical semantics from the semantic database 430, and determining a relevant semantic for the anatomical structure, based upon the label;

Determining the searchable attribute is preferably done using the classification method 501 according to the invention—this method is described in detail below. Typically, the models will be comprised in a database, so that the classification of the medical image 310 using one or more anatomical models may be performed prior to retrieval.

The retriever further comprises a user interface 330 for providing a user selection. Typically, the user input 330 provides for interaction with the system in any form known in the art, for example, as icons, thumbnails, menus, and pull-down menus. The user input 330 may also comprise a keyboard, mouse, trackball, pointer, drawing tablet or the like. The user input 330 may also provide speech recognition capabilities.

The retriever further comprises a processor 320. The processor 320 is configured to:

receive the user selection 380 of one of the anatomical semantics. The user interface 330 provides the user selection. This may be entered as keywords, text within a query, or by providing one or more semantic terms for the user to select. Selection by the user clicking on a displayed semantic term is also envisioned; and retrieve the medical image 310 using the user-selected semantic and the searchable attribute. Any conventional system may be employed to fetch the medical image 310 from the medical image database 410, and provide it to the user.

Figure 2:
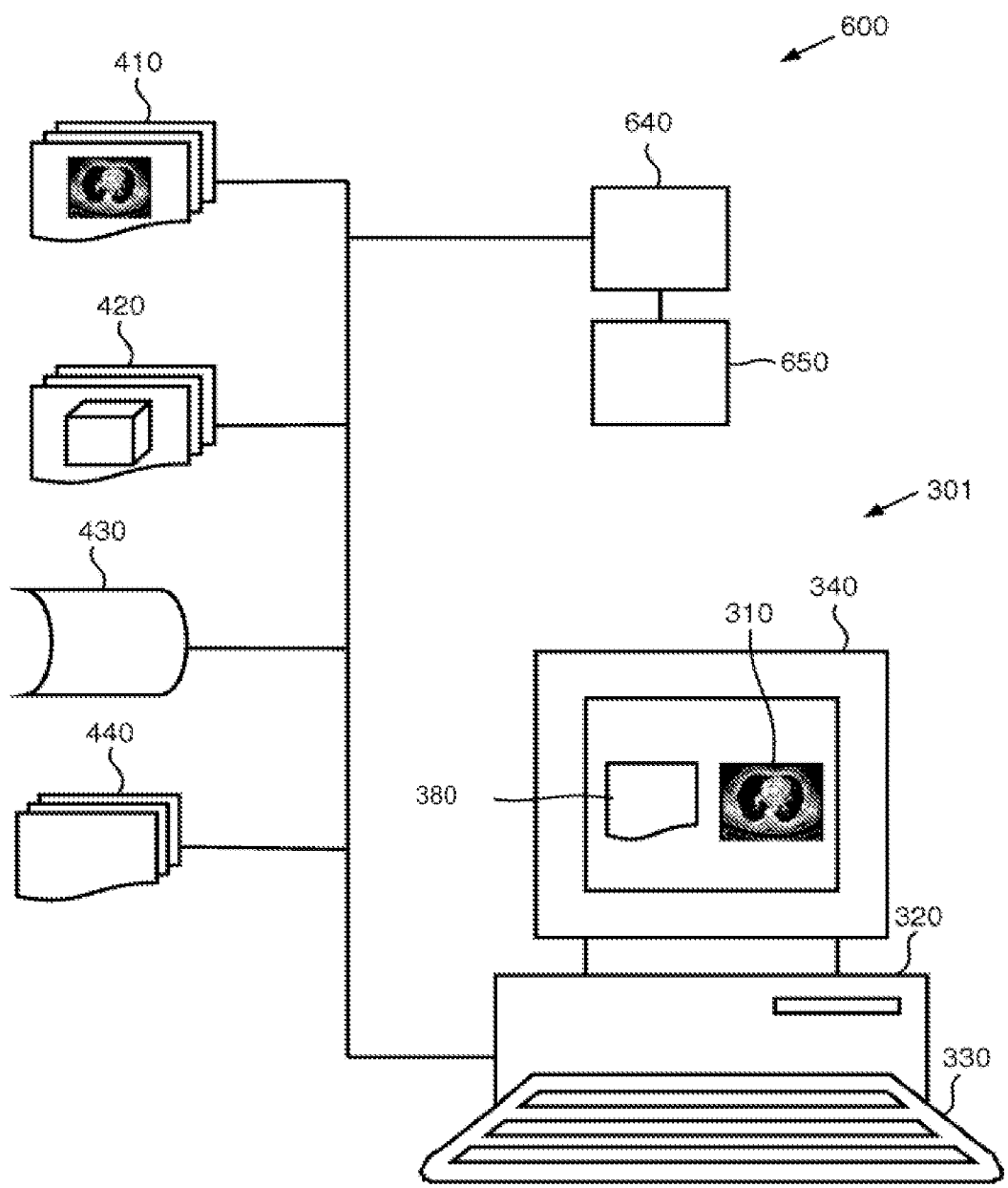
FIG. 2 depicts a second retriever and classifier according to the invention.
Figure 3:
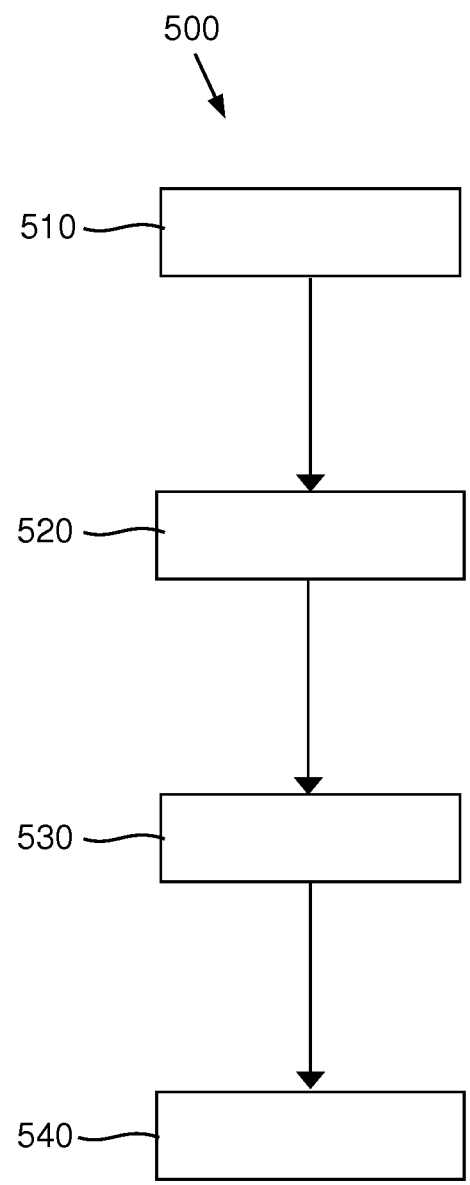
FIG. 3 depicts the method of retrieval according to the invention.
Figure 4:
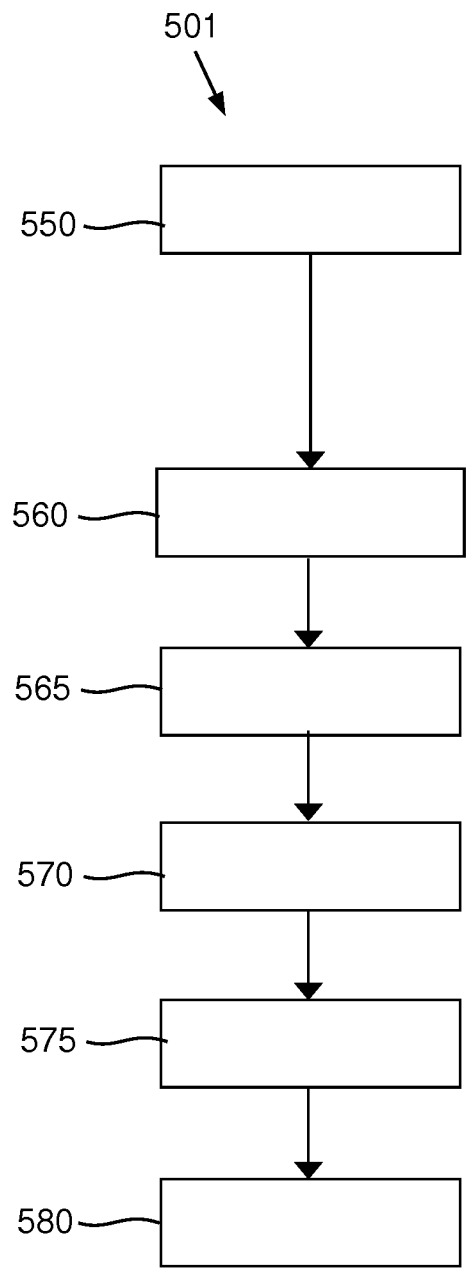
FIG. 4 depicts the method of classifying according to the invention.
Figure 5:
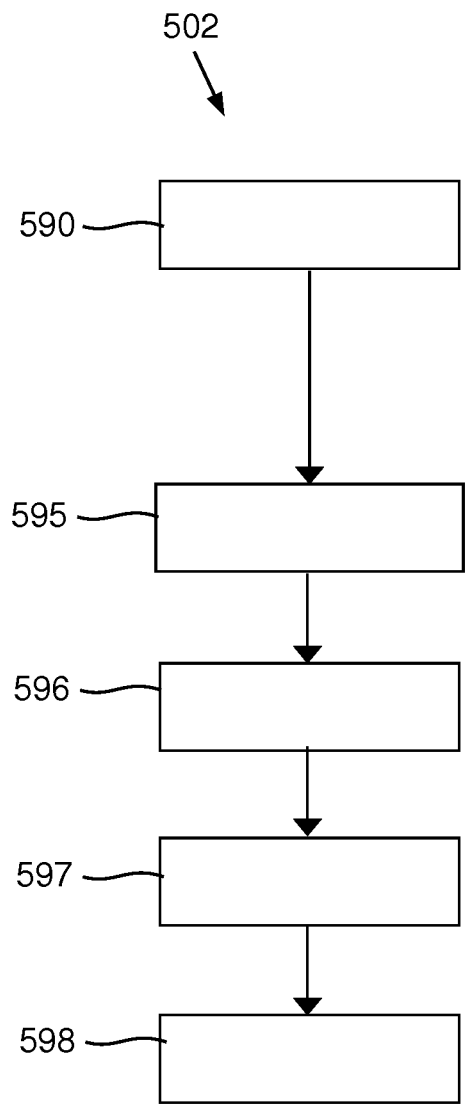
FIG. 5 depicts the method of distinguishing according to the invention.

The retriever 300 is configured for performing the retrieval method 500 according to the invention, which is depicted in FIG. 2. During operation, the following stages are performed:

providing 510 a semantic database 430, configured to store and provide anatomical semantics, and an image database 410, configured to store and provide the medical image 310;

classifying the medical image 310 by determining 520 the searchable attribute of the medical image. This is done by retrieving an anatomical model comprising a label associated with an anatomical structure; determining the presence of the anatomical structure by segmenting the medical image 310 using the anatomical model; retrieving anatomical semantics from the semantic database 430, and determining a relevant semantic for the anatomical structure based upon the label. These classification actions are described further below;

providing 530 a user selection 380 of one of the anatomical semantics, and retrieving 540 the medical image 310 using the user-selected semantic and the searchable attribute. The implementation of these actions depends on the relationship between the user-selected semantic and the searchable attribute, which also depends upon the semantic system selected.

For example, if a lexicon is used, this may be considered as a limited vocabulary that the user is forced to use in his queries and for his classification. For example, if "optical nerve" is comprised in the lexicon, then, if the user selects "optical nerve" as the semantic, a search will be made for any medical images with the attribute "optical nerve". In the simplest case, there will only be one image with this attribute, so it may be simply retrieved. Retrieval may be fully automatic, or subject to confirmation by the user.

In the case of a plurality of matches or hits, the user may be presented with a list for further selection, or an indication of the number of matches, so that he can refine his query, or a relevance may be calculated of all matches and the most relevant retrieved. Relevance may be calculated based upon attributes of the user known to the system, such as a profile, or other attributes of the medical image 310, or a combination of these.

Preferably, the matching algorithm is selected to deal with partial matches, so that the attributes "optical nerves" and "right optical nerve" will also be seen as a hit when the query semantic is "optic nerve". Also plurals may be interpreted explicitly, so the query semantic "optic nerves" may only match images which have both "right optical nerve" and "left optical nerve" as attributes. Alternatively, complex semantic queries may be accepted such as "right & left optical nerve". Matching may be implemented, for example, using string matching, sub-string matching or Levenstein-similarity matching.

If a hierarchical system of semantics or ontology is implemented, then a more intuitive matching system may be employed. For example, an anatomical hierarchy may provide for relationships between anatomical terms, such as part-of, extension-of, branch-of, synonym-of, adjacent-to, connected-to, symmetry-with, slice-with or encloses. These may be positional relationships, functional relationships or property relationships.

For example, the optical nerves may appear in different relationships, such as in a hierarchy of nerve functions:

Left retina (connected-to) left optical nerve (connected-to) visual cortex

Right retina (connected-to) right optical nerve (connected-to) visual cortex or a hierarchy of anatomical terms:

Left optical nerve (branch-of) central nervous system

Right optical nerve (branch-of) central nervous system or a hierarchy of positions:

Left optical nerve (adjacent to) cavernous sinus

Left optical nerve (adjacent-to) left lacrimal gland

Right optical nerve (adjacent to) cavernous sinus

Right optical nerve (adjacent-to) right lacrimal gland or a second hierarchy of positions:

Left optical nerve (adjacent to) left globe

Left optical nerve (adjacent to) left extraocular muscle

Right optical nerve (adjacent to) right globe

Right optical nerve (adjacent to) right extraocular muscle or a third hierarchy of positions:

skull (encloses) left orbit (encloses) left globe skull (encloses) right orbit (encloses) right globe As the medical images typically represent slices, it may be advantageous to link anatomical objects which typically appear in the same slice. It may also be advantageous to indicate if this is a transverse or longitudinal slice. Similarly, the indication that an anatomical object has a symmetrical partner may also be used as an indication that they are likely to appear in the same medical image. For example:

Left optical nerve (slice-with) right optical nerve

Left optical nerve (transverse slice-with) right optical nerve

Left globe (symmetry-with) right globe

It will be apparent to the skilled person that any combination of such relationships may be used, and that each anatomical term may be associated with a plurality of relationships. For example, skull (encloses) left orbit (encloses) left globe (encloses) left retina skull (encloses) left optical nerve visual cortex (connected to) left optical nerve (connected to) retina left orbit (symmetry-with) right orbit By using such relationships, the skilled person can configure the searching algorithm such that the semantic term "orbit" in a search query will match with "left globe" and "right globe" attributes for a medical image.

Relationships also facilitate a possible solution when no hits are encountered. Traditionally, this would be reported back to the user as "no hits found", leaving the user to broaden the query himself. However, by using the relationships, the algorithm may be constructed such that when a search finds no matches, the search is automatically repeated moving one step higher in the hierarchy. For example, the search semantic "lacrimal gland" may return no hits. The search algorithm would then move up to "orbit" because "orbit" (encloses) "lacrimal gland", and search for the attribute orbit. If still no hits are found the algorithm may either stop, alert the user, or move up higher in the hierarchy.

Preferably, this retrieval method is performed by the retriever 300 according to the invention. However, any system configured to perform this retrieval method may be employed.

The user input 330 may also provide the medical reports. In that case, the user input 330 will typically cooperate with a processor 320 to provide report handling functions, such as editing and word-processing facilities.

The skilled person will be able to find examples in the art to assist him in the implementation. For example, the article "MoSearch: A radiologist-friendly tool for finding-based diagnostic report and image retrieval", by Ramaswamy, Patterson, Yin, Goodacre (RSNA 1996); Radiographics 1996, 16, pages 923-933, discloses a software package that allows radiologists to conduct sophisticated real-time searches of diagnostic medical reports on the basis of patient characteristics, modality used, anatomy examined, and imaging findings and to easily review, refine, and output the results. A notable feature of this system is the use of synonym-matching and syntactic cues, which allow identifying findings within the text of a diagnostic report much more accurately than a simple keyword search. This type of system is easily and inexpensively implemented on a personal computer.

This article also describes other techniques known to the skilled person, such as coding the reports, structured report entry according to a prescribed format, natural language processing of the text in the reports, simple or complex keyword searches.

The skilled person will also be familiar with other search algorithms used by Internet search engines to determine relevance, such as www.google.com and www.yahoo.com, where the relevance is translated to a ranked list of hits.

Figure 6A:
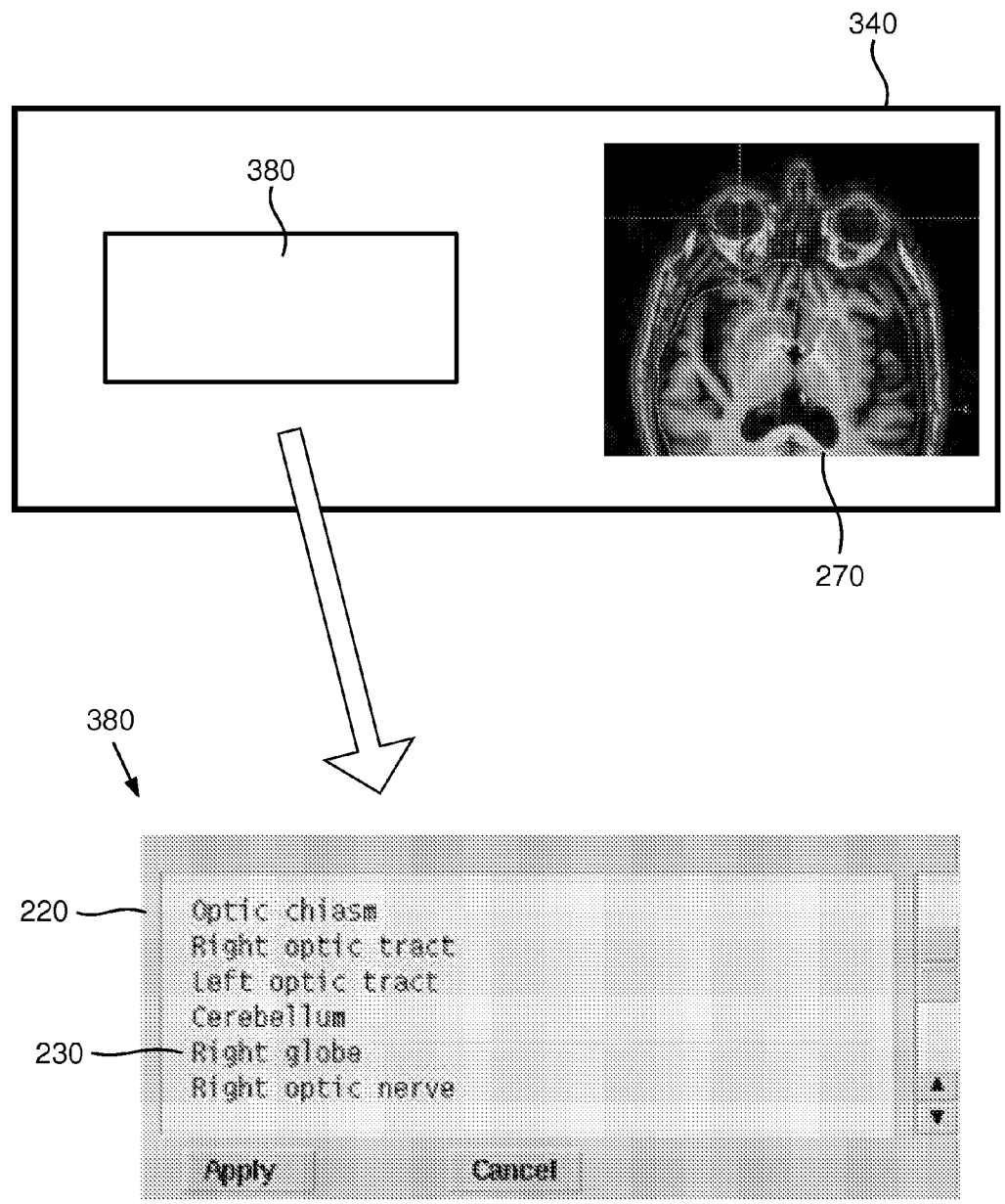

After retrieval of the medical image 310, the user will typically be provided with an appropriate representation on a display 340 of the retriever 300. FIG. 6A depicts a possible implementation of the representations which may be provided to the user. The display comprises a representation of the medical image 310 and a representation 380 comprising a menu 220 of anatomical semantics.

The semantic terms are retrieved from the semantic database 430, and presented to the user as a menu list 220. The user may then select 230 one or more of the terms. The retriever 300 will then search for a medical image with a matching or partially matching attribute, and display an appropriate representation 270 on the display 340. Optionally, a control may be provided for the user to initiate the search for a matching medical image.

FIG. 6B depicts a second possible implementation of the representations which may be provided to the user. The display comprises a representation of the medical image 310 and a representation 380 comprising the text 221 of a medical report, in which semantic terms have been distinguished from the rest of the text. Preferably, the semantic terms are distinguished according to the distinguishing method 502 described below.

The semantic terms distinguished in the medical report correspond to the semantic terms used to determine the search attribute of the medical image 310. Preferably, they are from the same database to ensure complete consistency.

Any convenient visual indication may be used to distinguish the semantic terms from the rest of the text for the user—for example bold letters 231, framing 232, 233 highlighting 234, underlining, using different colors, using a different font or character size, or blinking.

The user may then select one or more of the distinguished terms—this is most intuitively implemented by making the terms selectable or clickable, such as action boxes or hyperlinks. The retriever 300 will then search for a medical image with a matching or partially matching attribute, and display an appropriate representation 270 on the display 340. Optionally, a control may be provided for the user to initiate the search for a matching medical image.

The medical report 221 may be provided by the user and an algorithm run by the retriever to distinguish the terms. In that case, the retriever is preferably configured to perform the distinguishing method 502 described below. The distinguished report may then be stored in the medical report database 420.

Alternatively, the medical report 221 may be retrieved from a medical report database 420, where the terms were distinguished earlier, and the distinguishing properties stored with the report.

Optionally, a control means may be provided for the user to distinguish semantic terms in a currently opened medical report 221. It is also envisioned that such a control is integrated into a word-processing package, so that when a medical report 221 is saved in a buffer folder, the semantic terms are automatically distinguished.

Optionally, other control means 290 may provide other convenient functions to the user, such as allowing the user to manually specify distinguished terms, or to overrule the distinguishing of terms by the retriever 300.

It may be advantageous to process medical reports in the medical report database 420 prior to retrieval, so that the medical reports are stored with the terms distinguished and each term is associated with one or more medical images which were determined to be a match. Although this increases the complexity of medical report storage, processing may be done off line, and the computing power required by the retriever 300 is reduced.

It may be advantageous to determine a viewing attribute for the medical image 310, so that when the medical image is retrieved, the parameters of the representation 270 may be provided. These parameters may be automatically executed to produce the representation 270, or the user may be asked to confirm their execution. This greatly speeds up the viewing process for the user because he does not need to perform actions such as looking around the image for the desired anatomical structure, changing views, zooming in and out.

Generating a view for one or more anatomical structures, usually referred to as the Object-Of-Interest (OOI), is possible as follows. The segmentation software assigns all the voxels of the volume data set to objects for which a dedicated segmentation model has already been trained. Hence, it is possible to determine a bounding box around an object, so that all voxels assigned to this object are included. This bounding box may be uniquely identified by two points consisting of the minimum and maximum coordinates respectively of the object voxels. The software computes the bounding box around the object chosen, and uses this as a viewing attribute for the medical image 310, while the semantic term for the object is used as the searchable attribute.

Additionally, this may be used to provide multiple views for a single medical image 310 by determining different sets of viewing attributes associated with a searchable attribute. For example, for a medical image 310 depicting a transverse slice through the skull, three searchable sets of searchable attributes and viewing attributes may be determined:

searchable attribute: "left orbit"/viewing attribute: "20,100-80, 200"

searchable attribute: "right orbit"/viewing attribute: "120, 100-180, 200"

searchable attribute: "orbits"/viewing attribute: "20,100-180, 200".

Note that a simple X, Y coordinate system is used for this example. It will be apparent to the skilled person that any appropriate coordinate system may be used. For example:

In slice-based viewings, the voxel representing the OOI most, usually the geometric centre or centre of gravity point, is determined from the parameters of this box. This voxel serves as the centre point of the visualization and determines the slice number and the displacement of this slice so that the OOI is centered on the display 340. It is additionally possible to determine an optimal zooming attribute from the bounding box. The display 340 may then be configured to determine the display viewport size, so that the projection of the whole object fits into the viewport.

If a pure slice representation is not necessary, i.e. an oblique view meaning that the viewing angles from which the OOI is rendered may be varied, it is possible to determine the viewing angles so that the plane containing the plurality of voxels of the OOI is presented on the display. Additionally, object-specific landmarks can further help to optimize these view settings for the OOI.

In volume rendering-based representations like e.g. Direct Volume Rendering (DVR), Multi Planar Reformation (MPR) or Path Proximity Rendering (PPR), the segmentation of the OOI is used to produce a voxel mask or a path respectively that facilitates rendering the part that is included only within the mask or preferred voxels in closest proximity to that path.

The viewing attribute may be stored directly as part of the file—a textual title or an attribute or tag. Alternatively, the viewing attributes may be stored in a lookup table or file, comprising the viewing attribute with a file identifier. It is also envisioned that a lookup table is provided with standard view settings for particular semantics. However, this may only be advantageous if the image database is limited to images acquired in the same way, for example using the same modality. An intermediate embodiment is also envisioned, where an initial viewing attribute is provided, which may be modified based upon subsequent segmentation results.

As described above, a system and method are provided for retrieving classified medical images. A second aspect of the invention is the classification method 501 and a classifier 600 configured to perform the method 501.

The classifier 600 is configured to interface with:
an image database 410 configured to store and provide the medical image 310;
a semantic database 430 configured to store and provide anatomical semantics;
a model database 420 configured to store and provide an anatomical model, wherein the anatomical model comprises a label associated with an anatomical structure;

The classifier 600 comprises:
a segmenter 640 configured to:
retrieve an anatomical model comprising a label associated with an anatomical structure from the model database 420;
determine the presence of the anatomical structure by segmenting the medical image 310 using the anatomical model;
retrieve anatomical semantics from the semantic database 430;
determine a relevant semantic for the anatomical structure, based upon the label, and
store the medical image 310 in the image database 410, with the determined semantic being the searchable attribute of the medical image 310.

The classifier is configured for performing the classification method 501 according to the invention, the method comprising:
providing 550 an image database 410 configured to store and provide the medical image 310;
providing 550 a semantic database 430 configured to store and provide anatomical semantics;
providing 550 a model database 420 configured to store and provide an anatomical model, wherein the anatomical model comprises a label associated with an anatomical structure;
retrieving 560 an anatomical model comprising a label associated with an anatomical structure from the model database 420;
determining 565 the presence of the anatomical structure by segmenting the medical image 310 using the anatomical model;
retrieving 570 anatomical semantics from the semantic database 430;
determining 575 a relevant semantic for the anatomical structure, based upon the label, and
storing 580 the medical image 310 in the image database 410 with the determined semantic as the searchable attribute of the medical image 310.

The searchable attribute is most conveniently directly associated with the file comprising the image, for example as an attribute or tag. The searchable attribute may also be described in a separate look-up table or file, comprising the searchable attribute and an identifier of the file, such as a name, path or hyperlink.

In an alternative embodiment, the classification method 501 may be further modified to determine 575 the semantic, based upon text directly associated with the image. For example, an image may be given a title, or a description may be included in a file with the image, or the image file may comprise attributes or tags. This text may be used to help better define the semantic and may be more accurate. Semantics in this text are determined in a similar way to that used to distinguish semantics in the distinguishing method 502, explained below. The determination using any text directly associated with the image may be performed before or after determining 575 a relevant semantic for the anatomical structure, based upon the label. Prior thereto, segmentation of the image may be applied when the image is retrieved, to determine the view settings, and possibly to verify the accuracy of the classification performed earlier.

The classifier may be further configured for performing the distinguishing method 502 according to the invention, comprising:

providing 590 a report database 440, configured to store and provide medical reports;

retrieving 595 a medical report from the medical report database 440;

retrieving 596 anatomical semantics from the semantic database 430;

searching 597 the medical report for anatomical semantics and distinguish 231,232,233,234 the semantics found in the text 221, and storing 598 the medical report having distinguished semantics in the medical report database 440.

It is also envisioned that each semantic in the report is directly associated with a pointer to an image, so that it is not required to store semantics with the images. Such a pointer may be stored in the medical report, for example as a hyperlink, or in a separate look-up table or file, comprising a semantic and an identifier of the file, such as a name, path or hyperlink.

The skilled person, provided with the details of the method disclosed, will be able to implement numerous systems for performing the methods, in addition to the systems disclosed in this application. Typically, such a system will comprise a computer, and the skilled person will be able to assign the function to a combination of hardware and software, and consequently implement a computer program to carry out these methods, provided the computer program is loaded and run on the computer. For example, although a retriever and a classifier are described separately, they may be physically integrated into a single system.

A user may use a workstation to perform interactions, for example during the preparation of the medical report. The workstation may then comprise a processor 320 to distinguish the semantics in the text of the medical report so prepared. The workstation may then comprise the retriever according to the invention. It is also envisioned that the retriever 300 may be comprised in a medical image acquisition apparatus.

A user may use a workstation to perform interactions, for example during the maintenance of the database. The workstation may then comprise a segmenter 320 to determine the searchable attributes for one or more images in the image database. The workstation may then comprise the classifier according to the invention. It is also envisioned that the classifier 300 may be comprised in a medical image acquisition apparatus.

It will be apparent to the skilled person that a plurality of the functions of the system may be implemented in parallel, so that the same hardware may be utilized to provide a number of image and report databases. For example, it may be advantageous to limit a particular database to one particular discipline, such as radiology. This limits the choices available and reduces the risk of an incorrect semantic being used, thereby increasing the chance that a relevant image is obtained. A second database for a second discipline, such as pathology, may be provided in parallel, so that the semantic terms available may then be optimized for pathologists.

In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer.

The claims enumerate several functional blocks—a retriever, a user input, a processor, a display, a classifier, a segmenter, a distinguisher. Several of these means may be embodied by one and the same item of hardware. Additionally, one or more of the semantic, report, image and model databases may also be embodied. However, the skilled person will also be aware that remote or distributed databases may be employed in the invention.

The mere fact that certain measures are recited in mutually different dependent claims does not indicate that a combination of these measures cannot be used to advantage.

The invention claimed is:

1. A hardware-implemented retriever that retrieves a medical image having a searchable attribute, the retriever being configured to interface with:
   a semantic database configured to store and provide anatomical semantics,
   a model database configured to store anatomical models, wherein the semantic database and the model database are different databases; and
   an image database configured to store and provide the medical image, wherein the searchable attribute is determined by:
      retrieving, from the model database, an anatomical model, wherein the anatomical model comprises a label associated with an anatomical structure;
      determining a presence of the anatomical structure by segmenting at least one anatomical structure from the medical image using the anatomical model;
      retrieving anatomical semantics from the semantic database, and
      determining a relevant semantic for the at least one anatomical structure based upon the label;
   the retriever comprising:
      a user interface for providing a user selection, and
      a processor configured to:
         display a medical report of a patient on a display device and the medical report includes text with distinguished semantic terms and the distinguished semantic terms are selectable;
         in response to an input selecting one or more distinguished semantic terms from the displayed medical report text, retrieve the medical image with searchable attributes based on the one or more distinguished semantic terms;
         display the retrieved medical image according to one or more viewing attributes determined by a bounding box around the segmented structure and the bounding box includes all voxels of the segmented at least one anatomical structure, and the bounding box is identified by two points of segmented at least one anatomical structure, and the viewing attributes are generated based on the bounding box.

2. The retriever according to claim 1, wherein the distinguished semantic terms in the text of the medical report are distinguished for the user from the rest of the text of the medical report.

3. The retriever according to claim 2, wherein the user interface is configured to provide the medical report, the processor being further configured to:
   receive the medical report;
   retrieve anatomical semantics from the semantic database, and search the medical report for anatomical semantics and distinguish the semantics found in the text.

4. The retriever according to claim 1, wherein the anatomical semantics are organized as a hierarchy, lexicon or ontology.

5. A workstation or a medical imaging acquisition apparatus comprising the retriever according to claim 1.

6. The retriever according to claim 1, wherein the viewing attributes are user entered through the user interface and received by the retriever.

7. The retriever according to claim 1, wherein the generated viewing attributes of the segmented at least one anatomical structure includes at least one of:
   a selected image slice of a data volume;
   a viewing angle;
   a scaling;
   a rotation; and
   an initial zoom.

8. The retriever according to claim 7, wherein the processor is further configured to:
   determine a size of a display viewport such that a projection of the segmented at least one anatomical structure fits into the display viewport with the display of the retrieved at least one medical image.

9. The retriever according to claim 8, wherein the processor is further configured to:
   produce a voxel mask such that only the segmented at least one anatomical structure is rendered in the display of the retrieved at least one medical image.

10. A method of retrieving medical images, comprising:
    storing and providing anatomical semantics from a semantic database;
    storing anatomical models in a model database, wherein the semantic database and the model database are different databases;
    displaying a medical report of a patient on a display device and the medical report includes text with distinguished semantic terms and the distinguished semantic terms are selectable;
    in response to an input providing a user selection selecting one or more distinguished semantic terms from the displayed medical report text, retrieving the medical image from an image database that stores and provides medical images with searchable attributes based on the one or more distinguished semantic terms, wherein the searchable attributes are determined by retrieving, from the model database, an anatomical model, wherein the anatomical model comprises a label associated with an anatomical structure, determining a presence of the anatomical structure by segmenting at least one anatomical structure from the medical image using the anatomical model, retrieving anatomical semantics from the semantic database, and determining a relevant semantic for the at least one anatomical structure based upon the label;
    displaying the retrieved medical image on the display device according to one or more viewing attributes; and
    wherein the viewing attributes are determined for the medical image by determining a bounding box around the segmented structure and the bounding box includes all voxels of the segmented at least one anatomical structure, and the bounding box is identified by two points of segmented at least one anatomical structure, and the viewing attributes are generated based on the bounding box.

11. The method according to claim 10, wherein the viewing attributes are user entered through the user interface and received by the retriever.

12. The method according to claim 10, wherein the generated viewing attributes of the segmented at least one anatomical structure includes at least one of:
    a selected image slice of a data volume;
    a viewing angle;
    a scaling;
    a rotation; and
    an initial zoom.

13. The method according to claim 10, wherein displaying includes:
    determining a size of a display viewport such that a projection of the segmented at least one anatomical structure fits into the display viewport with the display of the retrieved medical image.

14. The method according to claim 10, wherein displaying includes:
    producing a voxel mask such that only the segmented at least one anatomical structure is rendered in the display of the retrieved medical image.

* * * * *